(12) United States Patent
Nentwich

(10) Patent No.: US 9,720,406 B2
(45) Date of Patent: Aug. 1, 2017

(54) MEASURING SYSTEM

(75) Inventor: Jessica Nentwich, Korntal-Munchingen (DE)

(73) Assignee: Endress+Hauser Conducta GmbH+Co. KG, Gerlingen (DE)

(*) Notice: Subject to any disclaimer, the term of this patent is extended or adjusted under 35 U.S.C. 154(b) by 728 days.

(21) Appl. No.: 13/585,105

(22) Filed: Aug. 14, 2012

(65) Prior Publication Data

US 2013/0046501 A1 Feb. 21, 2013

Related U.S. Application Data

(60) Provisional application No. 61/523,457, filed on Aug. 15, 2011.

(51) Int. Cl.
*G05B 21/02* (2006.01)
*G01N 27/30* (2006.01)

(52) U.S. Cl.
CPC ............. *G05B 21/02* (2013.01); *G01N 27/30* (2013.01)

(58) Field of Classification Search
CPC .... G01N 27/4165; G01N 27/30; G05B 21/02; G06F 19/00
See application file for complete search history.

(56) References Cited

U.S. PATENT DOCUMENTS

| | | | |
|---|---|---|---|
| 2003/0130805 A1* | 7/2003 | Wittmer et al. | 702/31 |
| 2006/0167643 A1* | 7/2006 | Casto et al. | 702/85 |
| 2009/0131650 A1* | 5/2009 | Brahmasandra et al. | 536/25.4 |
| 2009/0287445 A1* | 11/2009 | Vayhinger | 702/100 |

* cited by examiner

*Primary Examiner* — Manuel Rivera Vargas
(74) *Attorney, Agent, or Firm* — Mark A. Logan; PatServe

(57) ABSTRACT

A measuring system including: at least one sensor module having a measuring transducer and an electronics module. The electronics module has a data memory, and a superordinated control unit, connected to the at least one sensor module via an interface module. The interface module has a signal processing, and communication, electronics, which converts received signals from a control unit into signals processable by the sensor module and outputs these signals to the sensor module. The control unit is embodied to execute an operating program; the operating program is embodied to read out sensor specific data and, based on the data read out, to provide to a user a guiding through a sequence of steps for performing at least one calibration procedure associated with the sensor module and to operate the sensor module for performing the calibration procedure.

22 Claims, 9 Drawing Sheets

Fig. 4

| Sensor Details | | |
|---|---|---|
| Name | CPS 11D | Startup Date  11/07/20 |
| Code | CPS 11D-7BA21 | Deactivation |
| Serial Number | 9A007A05E00 | |

| Installation Location | | |
|---|---|---|
| Template Type | Sensor - Template | ▶ |
| Template Name | pH Glas 1 | |
| Operation | Calibration Method | ▶ |
| Plant | ☑ Display Calibration Reminder | |
| Cost Center | 20 ▲▼ Days since last calibration | |
| Measuring Point | ☑ Automatic E-mail Reminder | |
| Measuring Point Tag | | |
| Tag Group | | |

Measure
Calibrate
Sensors
Settings
Sensor information
Sensor Management
Reports
Setup
Help

| Quit | Save | Save settings in new template | Delete Template | Back |

Labels: 206, 202, 204, 205, 201, 203

MEASURING SYSTEM

CROSS-REFERENCE TO RELATED APPLICATION

This application is a Nonprovisional application, claiming the benefit of U.S. Provisional Application 61/523,457, filed on Aug. 15, 2011.

TECHNICAL FIELD

The invention relates to a measuring system having at least one sensor module, which includes a measuring transducer and an electronics module, wherein the electronics module has a data memory, in which sensor specific data are stored, and having a superordinated control unit connected to the at least one sensor module via an interface module. Generally, the control unit can be a data processing unit, for example, a PC or a portable computer such as a laptop, handheld, smart phone, tablet computer or iPod having a display apparatus, and an input system, for example, a keyboard or touch screen.

The interface module includes a signal processing, and communication, electronics, which converts the received signals from the at least one sensor module into signals processable by the control unit and outputs these to the control unit and converts the received signals from the control unit into signals processable by the sensor module and outputs these to the sensor module.

BACKGROUND DISCUSSION

In process measurements technology and in laboratory applications, the measuring and monitoring of the physical or chemical parameters of process media or media used in laboratory experiments plays an important role. Such parameters are, for example, pH value, temperature, conductivity, redox potentials, turbidity, oxygen concentration or oxygen partial pressure, ion concentrations, nutrient concentrations, nitrate or chlorine concentrations or concentrations other of chemical compounds. Frequently, sensor modules that must be maintained from time to time are used for measuring these and other parameters. After a maintenance procedure, such as a regenerating, calibration or adjusting, the sensor modules can be used further.

Many such sensor modules are applied in a process in industry, for example, the chemical industry, food technology and the pharmaceuticals industry. The sensor modules are frequently connected to a superordinated unit, for example, a measurement transmitter or a bus coupler, which is arranged near the measuring point and serves for the operation of the sensor unit and for registering, representing, or outputting and, in given cases, forwarding the measurement results to a process control system. Here, there is the need for a function monitoring of each of these sensor modules in order to assure that required maintenance measures can be planned and performed sufficiently early that, at any time, adequate accuracy of measurement of the sensor modules is assured and the process to be controlled by the sensor modules is not endangered. In many areas, especially the food industry and pharmaceuticals industry, it is required, moreover, to have detailed documentation of all aspects of a production process. This also includes the documentation of both the function monitoring as well as the maintenance measures for sensor modules, which are used for monitoring and checking the production process. Furthermore, in the servicing and maintaining of the sensor modules, the risk of servicing errors should be as small as possible.

Maintenance measures, especially such as calibration and/or adjusting, for the sensor modules are frequently not performed directly at the measuring point, at which the respective sensor modules are applied in a process, but centrally in the laboratory.

A measuring system having a superordinated control unit and at least one intelligent field device, which can be, for example, a sensor module, connectable to the control unit is known from DE 20 2010 016 362 U1; this measuring system can be used, on the one hand, for performing measurements by means of the field device, and on the other hand, for performing calibrations on the field device and/or adjusting the field device. Associated with the control unit is at least one interface with a connection element for accommodating a corresponding connection counterpart, wherein the connection counterpart is associated with an interface module, wherein associated with the interface module is a software protection system securing access to the field device, wherein the interface module permits communication between the corresponding field device and the superordinated control unit, wherein associated with the superordinated control unit is a software protected editing program for the field device, and wherein the editing program is started or enabled via the software protection system when the connection counterpart of the interface module of the field device is connected to the connection element of the control unit. As soon as the interface module is connected to the control unit, the editing program associated with the field device starts. The editing program is embodied to graphically represent measurement data transmitted by the field device on a display of the control unit or to execute a parametering/configuring of the field device via the control unit. The measuring system of DE 20 2010 016 362 U1 also permits, for calibration purposes, the connection, in addition to the actual field device, of a reference field device for reviewing the measured values of the actual field device.

US 2009/0287445 A1 describes a system for calibration and function checking a sensor system used in a process. The sensor system can be a measuring probe with a sensor module, a memory system and an electronic input/output interface, wherein the memory system communicates both with the sensor module as well as with the input/output interface. The sensor module can be connected to a PC, which is arranged remotely from the process, or to a measurement transmitter arranged near the process. The PC can utilize operating software for calibration and function checking the sensor module. Both the measurement transmitter as well as the operating software can access a central database, in which information on sensor modules is stored. The operating software is embodied to calibrate the sensor module connected to the PC. For this, a user must handle the sensor module to be calibrated, for example, to clean and to immerse it in at least one calibration medium, on the one hand, and, on the other hand, to input a series of calibration parameters, for example, the identification numbers of the calibration media used for calibration, in an entry form of the operating program. In more complex calibration procedures, for example, in calibrations, which include the registering of a series of measurement points in different calibration and/or reference media, errors can easily occur with a user lacks sufficient training or experience. Likewise, errors can occur in the inputting of parameters of the calibration media or sensor specific data. Moreover, inputting data or setup information in an operating program requires a certain expenditure of time.

SUMMARY OF THE INVENTION

It is, therefore, an object of the present invention to provide a measuring system, which overcomes the disadvantages of the state of the art. Especially, the measuring system should permit a simple, time saving, less error susceptible performing of maintenance measures, especially calibrations and/or adjustments, for sensor modules and a detailed documentation of the maintenance measures, especially calibration results. Furthermore, the measuring system should assure a reliable function monitoring and managing of sensor modules and be as user friendly as possible.

This object is achieved by a measuring system including: at least one sensor module having a measuring transducer and an electronics module, wherein the electronics module has a data memory, in which sensor specific data are stored; and a superordinated control unit, especially a PC or laptop, having a display apparatus, for example, a display, and an input system, for example, a keyboard, and connected with the at least one sensor module via an interface module; wherein the interface module has a signal processing, and communication, electronics, which converts received signals from the at least one sensor module into signals processable by the control unit and outputs these signals to the control unit and converts received signals from the control unit into signals processable by the sensor module and outputs these signals to the sensor module; wherein the control unit is embodied to execute an operating program for the at least one sensor module; the operating program is embodied to read out sensor specific data from the data memory of the sensor module and, based on the data read out, to provide to a user a guiding through a sequence of steps for performing at least one calibration procedure associated with the sensor module and to operate the sensor module for performing the calibration procedure.

The operating program can be supplementally embodied to store data in the data memory of the sensor module. For example, for the adjustment of the sensor module, data, such as the zero point and slope of the sensor module characteristic line based on the characteristic line data ascertained by means of the operating program, can be written into the data memory. Other information for sensor management can also be written into the data memory.

The interface module can be connected to the control unit, for example, via a USB interface. The interface module can be connected to the sensor module via a cable connection and/or a plug contact. The sensor module can be, for example, one of the intelligent sensor modules having the Memosens interface available from the assignee. Such sensor modules can be pH sensors, conductivity sensors, oxygen sensors, chlorine sensors, nitrate sensors, redox sensors, ion selective electrodes or turbidity sensors. These sensor modules have a primary side of a plugged connection, into which a sensor electronics having a data memory and a microcontroller is integrated. In addition to sensor specific data such as serial number, measuring point tag, point in time of start up, point in time of the most recent calibration, operating hours etc., the calibration results of the most recent calibration, especially the zero point or offset and slope of a characteristic line of the sensor module ascertained in the most recent calibration can also be stored in the data memory of a sensor module. The primary side of the plugged connection can be coupled to a secondary side, which, in turn, can be connected to the interface module via a cable connection. The interface module can be embodied to convert the protocol, which is proprietary in given cases, of the sensor modules to a protocol used by the control unit, for example, the USB protocol, so that a computer serving as a control unit can communicate with the sensor module via the interface module and can service the sensor module. Servicing the sensor module is especially understood as the reading out of data from the data memory of the sensor module, the writing of data into the data memory of the sensor module, the receiving and processing of measurement signals of the sensor module and the sending of information, e.g. control signals, from the control unit to the sensor module for parametering or for performing measurements.

In an especially preferred embodiment of the measuring system, a plurality of interface modules and/or a plurality of sensor modules can be connectable to the superordinated control unit, so that a measurement channel is associated with each sensor module connected to the control unit, and wherein the operating program is embodied to operate the measurement channels in parallel. In this case, the measuring system is a multichannel measuring system.

For example, the operating program can be multiply instantiable and each instance of the operating program can be embodied for servicing one of the plurality of interface modules, so that the plurality of sensor modules can be serviced simultaneously. For example, a split screen representation can be provided so that data for each of the connected sensor modules can be displayed on the display of the control unit simultaneously. In this way, a number of sensor modules can be operated simultaneously, for example, for performing measurements or for performing a calibration. Of course, a non-multiply instantiated operating program can also be provided for multichannel measuring (known as true multichannel capability).

The simultaneously operated sensor modules need not necessarily be suitable for measuring one and the same parameter. Rather, it is also possible that at least two of the simultaneously operated sensor modules measure different parameters so that the measuring system can be operated as a multichannel multi-parameter measuring system. For example, a pH sensor module, a conductivity sensor module, a dissolved oxygen sensor module and a redox sensor module can be operated simultaneously with any combination of functionalities.

If a sensor module is connected to the control unit via the interface module for performing a calibration and, in given cases, for adjusting, the operating program can read out data from the data memory of the sensor module. The read out data can be, for example, a sensor identification. Based on the sensor identification, the operating program can, with the read out sensor identification identify, one or more stored settings, e.g. calibration procedures, for the sensor module and provide a user with a guiding through a sequence of steps of the calibration procedures. If a number of calibration procedures are available for a sensor module identified based on the read out sensor identification, the user can select one of the calibration procedures via a selection menu. If the sensor module is, for example, a potentiometric pH sensor with a glass electrode, the operating program can offer the user, for example, a 1 point calibration with a buffer solution as the calibration medium, a 2 point calibration with two buffer solutions having different pH values as the calibration media and/or a 2 point calibration with an "as found" measuring preceding the calibration and an "as left" measuring following the calibration. If it is, in contrast, a conductivity sensor, the operating program can automatically offer to the user, for example, a 1 point calibration using a reference conductivity medium suitable to this sensor type.

In an advantageous embodiment, the measuring system supplementally includes a database, wherein the operating program is embodied to access data stored in the database and/or to store data in the database.

The operating program can include at least one entry form serving to manage sensor modules; information and specifications for individual sensor modules and/or for a group of sensor modules can be input into the entry form. The inputs can be stored in the database for one sensor module or for a group of sensor modules. For example, a sensor module can be associated with a name for the measuring point, on which the sensor module is applied. A preferred calibration procedure, which should be applied regularly for calibration of the sensor module, can also be specified. In this case, the operating software offers the user this stored calibration procedure for the sensor module automatically.

The length of the calibration interval desired for the particular sensor module, i.e. the time span between two calibrations, can also be fixed via the entry form. Based on this information, the operating program can be embodied to send the user a reminder for the next scheduled calibration of a sensor module. For this, the user can select between different options: For example, the operating program can create and output, for predetermined points in time, e.g. once daily, a list of all active sensor modules, wherein the point in time of the next scheduled calibration is given in the list. Alternatively, the operating program can generate an email, in which the next scheduled calibrations are noted, and transmit this to a predetermined email address or to another system outside of the operating program.

The operating program can also be embodied to create templates for an individual sensor module or for an entire group of sensor modules, e.g. for a specific sensor type or for sensor modules, which are used in a specific process, especially at one and the same measuring point. Such a template can contain the above named settings, thus the preferred calibration procedure, the desired calibration interval, inputs for the reminder of the next scheduled calibration as well as information concerning the measuring point.

At least one of the steps for performing a calibration procedure can require an input via the input system by the user, wherein the operating program is embodied to operate the sensor module based on the input.

A calibration procedure can comprise the performing of at least one calibration measurement with the sensor module in a calibration medium, for example, a buffer liquid, wherein the operating program is embodied to represent the measurement signal output by the sensor module during the calibration measurement as a function of time in the form of a two dimensional or multidimensional graph by means of the display device. Based on the speed with which the measurement signal approaches the measured value of the calibration medium, an experienced user can draw important conclusions in reference to the state, especially the remaining service life, of the sensor module. This so called transient behavior of the sensor module is, as a rule, a measure for the age of the sensor module or for the extent of the loadings, which the sensor module has already experienced during its operating time.

The operating program can be embodied to perform steps as follows:
displaying a request to specify a first and a second calibration medium;
displaying a request to clean the sensor module and to bring it in contact with the first calibration medium;
performing a first calibration measurement, especially based on an input of the user;
displaying and storing calibration data after terminating the first calibration measurement, especially calibration measured value, response time, temperature of the calibration medium and point in time of the first calibration measurement;
displaying a request to bring the sensor module in contact with the second calibration medium;
performing a second calibration measurement, especially based on an input of the user;
displaying and storing the calibration data after terminating the second calibration measurement, especially calibration measured value, response time, temperature of the calibration medium and point in time of the second calibration measurement.

The calibration data can be stored in the database and/or in the data memory of the sensor module.

The operating program can furthermore be embodied to determine, upon an input of the user, a zero point and a slope of a characteristic line of the sensor module based on the calibration data registered in the first and second calibration measurements. The zero point and the slope can be stored in the database and/or in the data memory of the sensor module. Preferably, the stored values are associated with the point in time of the current calibration, so that a calibration history can be derived from the values stored in the database or the values of a zero point and slope from different calibrations stored in the data memory of the sensor module and can be presented graphically. The operating program can furthermore be embodied to adjust the sensor module, wherein the adjusting includes adapting the characteristic line of the sensor module stored in the data memory by means of the newly ascertained values of zero point and slope.

The operating program can be embodied, in the case of selection of a calibration procedure, which comprises an "as found"/"as left" measuring, to prompt the user, before the cleaning and the performing of the first calibration measurement, to perform a first measuring in at least one reference medium and, after performing the first calibration measurement and adjusting the sensor module, to perform a second measuring in the at least one reference medium, wherein the results of the first and second measurements in the at least one reference medium are stored in the database.

The operating program can be embodied, in the case of connecting a sensor module via the interface module to the control unit, to compare calibration data stored in the sensor module with the calibration data stored in the database for this sensor module and in the case of finding unknown calibration data, i.e. calibration data not stored in the database, to input the unknown calibration data into the database, especially after confirmation by the user.

The specification of the first and/or the second calibration medium can occur by selecting a calibration medium from a calibration media list, wherein the operating program has an entry form embodied for managing calibration media; a calibration media designation, an expiration date of the calibration medium and, in given cases, other information for each calibration medium can be input into the entry form, and wherein it can be provided that after exceeding the expiration date of the calibration medium, the calibration medium should automatically be removed from the calibration media list. Alternatively, it can be provided that after exceeding the expiration date, the name of the calibration medium in the calibration media list is provided with a colored background or characterized graphically some other manner.

The operating program can be embodied to create a list based on information for sensor management stored in the database; which sensor modules next in time to be calibrated as well as the next calibration point in time for these sensor modules are stated in the list. Preferably, the sensor modules set forth in the list are sorted in decreasing order according to the point in time of the calibration. The operating program can be embodied to transmit the list to a stored email address or to another information system.

The operating program can be embodied, upon request by the user, to compile data and/or data histories stored in the database and/or in the memory of the connected sensor module in a report, for example, a measurement report, sensor report or calibration report, and to output the report as a storable and/or printable file.

A calibration report can include the point in time of the most recent calibration, the results of the most recent calibration measurement, the calibration data, and a graphical representation of the characteristic line of the sensor module ascertained based on the most recent calibration measurement, especially the values for the zero point and slope of the characteristic line most recently ascertained. Preferably, the calibration report can also include the changes since the calibration preceding the most recent calibration, thus, for example, the change of the values of zero point and slope. It is also possible to indicate all values of the zero point and slope registered over the period of use of the sensor module and stored in the database as a function of time so that a graphical representation of the curve of the zero point and slope over the operating time of the sensor module is obtained. From this curve an experienced user can estimate the remaining operating time ("lifetime") of the sensor module.

If desired by the user, the curve of the zero point and slope over the operating time of a group of sensor modules, for example, all sensor modules, which are associated with a determined measuring point, can also be displayed, for example, graphically. Therefrom, a user can draw conclusions about the lifetime of sensor modules at a certain measuring point.

The operating program can also be embodied to operate the at least one sensor module, preferably all sensor modules connected to the control unit, in a measurement operation, wherein the user can choose between a continuous measuring operation and a standard measurement operation, in which a measuring interval having a beginning and an end point in time is able to be fixed. If the measuring system has a number of sensor modules, each of which is associated with a measurement channel, the operating program can preferably perform parallel measurements in all measuring channels, especially multichannel, multi-parameter measurements as described above.

The operating program can furthermore be embodied to represent measured value development in measurement operation in a 2 or 3 dimensional graph.

BRIEF DESCRIPTION OF THE DRAWINGS

The invention will now be described in greater detail based on the examples shown in the drawing, the figures of which show as follows:

FIG. 4 is a display of the sensor management of the operating program;

DETAILED DESCRIPTION IN CONJUNCTION WITH THE DRAWINGS

Figure 1:
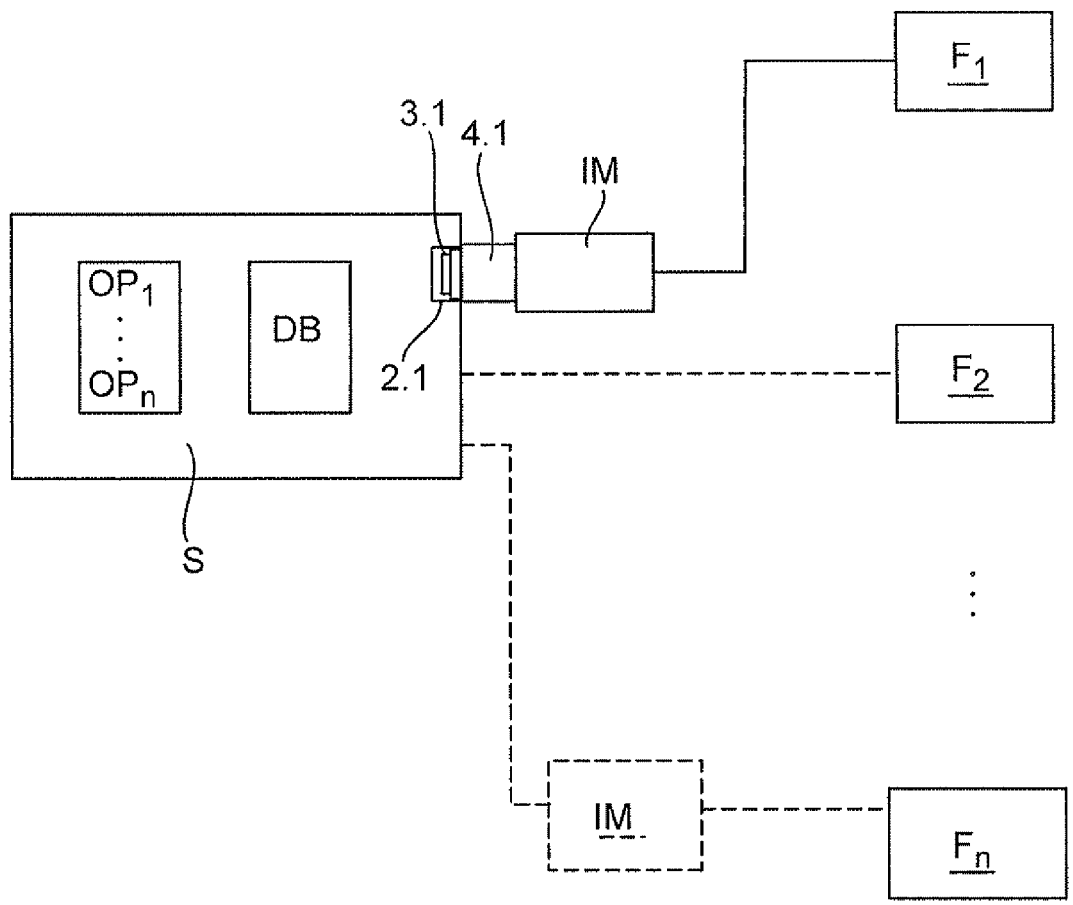
FIG. 1 is a measuring system of the invention having a control unit and a number of sensor modules connected to the control unit via interface modules.

FIG. 1 shows, schematically, an example of an embodiment of the measuring system. The measuring system includes a control unit S and a number of intelligent sensor modules F1, F2 . . . Fn connected to control unit S. The intelligent sensor modules F1, F2 . . . Fn include a measuring transducer for registering a physical or chemical parameter of a measured medium, and a sensor electronics for processing the measuring signals produced by the measuring transducer. The sensor electronics can include at least one microcontroller and at least one data memory, which the microcontroller can access. Of course, the measuring system can have only a single sensor module F1 connected to the control unit.

Associated with control unit S is at least one interface 2.1. For example, a computer, e.g. a PC or a laptop, can serve as control unit S. A USB interface can serve as interface 2.1, in this case. An interface module IM is connectable to interface 2.1 via a connector 3.1 and a cable 4.1. Interface module IM is connected to sensor module F1 via another cable. If the measuring system includes a number of sensor modules F1, F2 . . . Fn, then these can either be connected to interface 2.1 of control unit S via an interface module embodied as a hub, or each sensor module F1, F2 . . . Fn can be connected to its own interface module IM, each of which has its own interface, for example, a USB interface, in control unit S. Instead of cables between sensor modules F1, F2 . . . Fn and interface modules IM, or between interface modules IM and control unit S, wireless connections can also be provided, via which communication and, in given cases, energy transmission can occur.

Interface modules IM are embodied to convert signals from the sensor modules F1, F2 . . . Fn into signals processable by control unit S and to forward these signals to control unit S for processing, or to convert signals, especially control signals, from control unit S into signals processable by sensor modules F1, F2 . . . Fn and to output these to sensor modules F1, F2 . . . Fn. Via the interface modules, the control unit can especially access the data memory of sensor modules F1, F2 . . . Fn, in order to read out or store data.

Such a measuring system can be used for tasks as follows: For performing measurements with the sensor modules; for the representation, storing and further processing of measured values received from the sensor modules; for performing calibration measurements with the sensor modules and for adjusting the sensor modules; as well as for the representation, storing, further processing and managing of calibration data, sensor data, measuring point data and additional information for the sensor modules. For this, the measuring system includes operating program B1 . . . Bn executable by control unit S; operating program OP1 . . . OPn can process data read out from sensor modules F1, F2 . . . Fn and store this data in a data memory of control unit S. Operating program OP1 . . . OPn can, moreover, also output data for transmission to sensor modules F1, F2 . . . Fn and for storing in the data memories of sensor modules F1, F2 . . . Fn. Operating program OP1 . . . OPn can also be embodied to output control commands to sensor modules F1, F2 . . . Fn via interface module IM in order to service these sensor modules. Alternatively, with one instance of the operating program B1 can also be simultaneously associated a plurality of sensor modules F1, F2 . . . Fn (true multi-channel capability).

If a number of sensor modules F1, F2 . . . Fn are present, control unit S can produce and operate a number of instances OP1 . . . OPn of the operating program, wherein each sensor module F1, F2 . . . Fn has its own instance. For example, the simultaneously operated instances can be presented on a display of the control unit, for example, a display or monitor, by means of a split screen representation or by means of a number of selectable tabs within a display window. In this way, it is possible to simultaneously perform measurements with a number of sensor modules. Especially, the sensor modules can be embodied for measuring different parameters; for example, pH value, dissolved oxygen content and conductivity or any other parameter combinations can be measured simultaneously by means of one control unit. Moreover, it is possible to simultaneously calibrate a number of sensor modules by means of the one and the same control unit. This permits a considerable efficiency improvement compared to systems known from the state of the art.

Furthermore, the measuring system includes a database DB, which is stored in a memory of control unit S in the example described here. In an alternative embodiment, however, it is also possible that control unit S, via a network connection, for example, the Internet or an intranet, accesses the database, which, for example, can be stored on a central server.

In the following, some functions of the measuring system and the operating program will now be described in detail based on some screen shots of the operating program.

Figure 2:
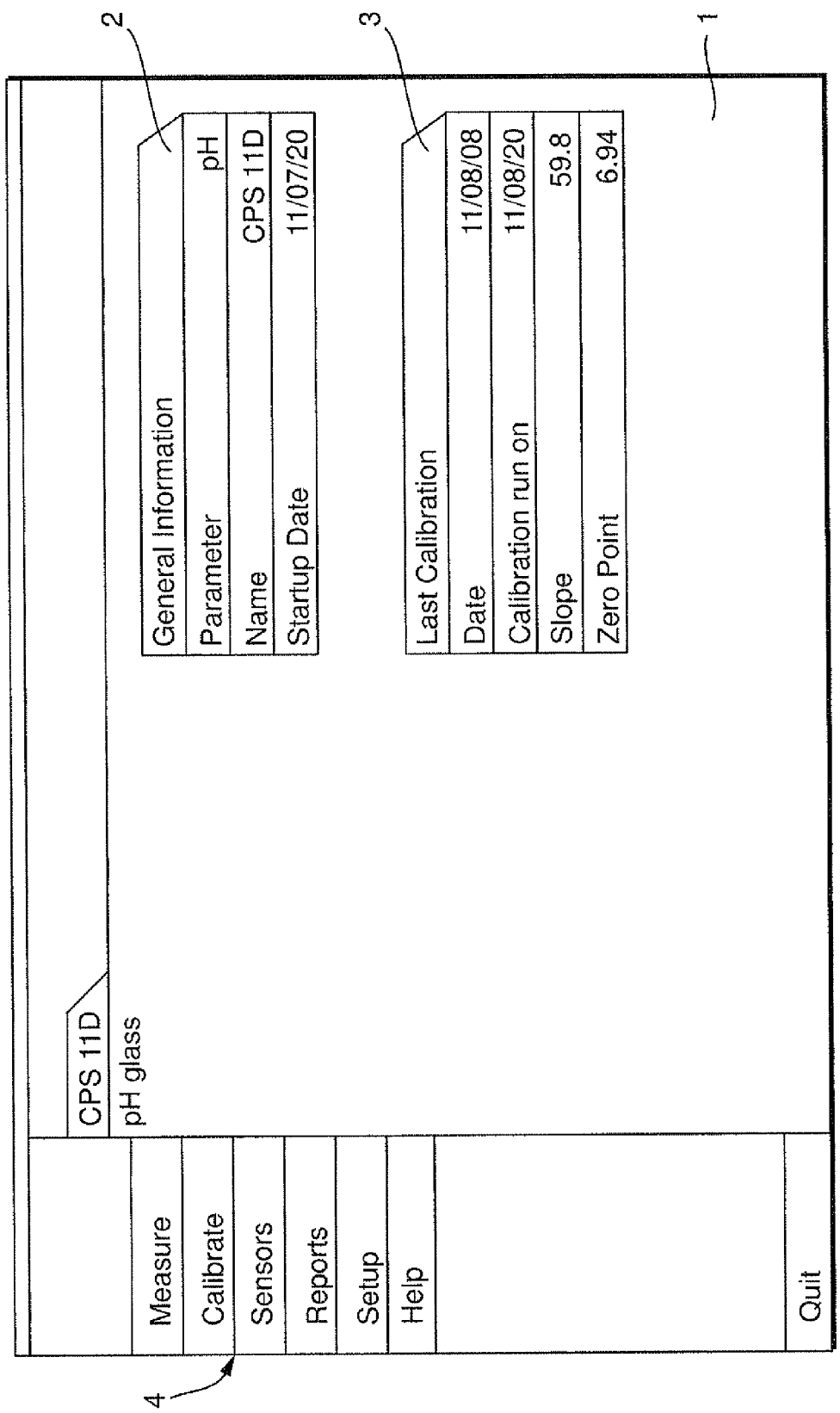
FIG. 2 is a display of the operating program executable by the control unit with data read out from a data memory of a sensor module.

With a connection of a sensor module to the control unit via an interface module, data stored in the data memory of the sensor module can be read out automatically by means of the operating program. FIG. 2 shows a first screen shot 1 of a view, in which some important information for the connected sensor module is displayed to a user. In the present example the sensor module is a pH glass electrode. The operating program reads specific identification data as well as data from past calibrations from the data memory of the sensor module. The sensor identification ascertained based on the data read out from the data memory of the sensor module is given on tab 5. "General information" for the connected sensor module, especially the sensor name, the point in time of the start up and the parameter registered by the sensor module, here the pH value, are given in an area 2. Other information can also be displayed. For example, the operating program can identify the sensor module based on the sensor name read out from the data memory of the sensor module or based on other identifying data of the sensor module and read out other data or information associated with the identified sensor module from database DB and can present the data in the overview. An area 3 presents data for the last calibration, especially the point in time of the last calibration, the point in time of the next scheduled calibration as well as the slope and zero point of the characteristic line of the sensor module ascertained during the last adjusting of the sensor module.

The user can invoke other operating program functions from a menu bar 4. A display of the measured values currently registered by the sensor module and other data relating to the measuring can be invoked via the menu point "Measuring". In this function mode the operating program can operate the sensor module as a measurement transmitter. This function mode is especially good for performing measurements in the laboratory, since it permits the performing of measurements with the sensor module without requiring an additional, expensive measurement transmitter for the operation of the sensor module.

Via the menu point "Sensors" of menu bar 4, a series of program functions for managing a number of sensor modules is available to the user. For example, the user can create templates, in which certain settings of the operating program can be fixed for a certain sensor module or for a group of sensor modules, for example, for sensors of a specific type or series.

Figure 3:
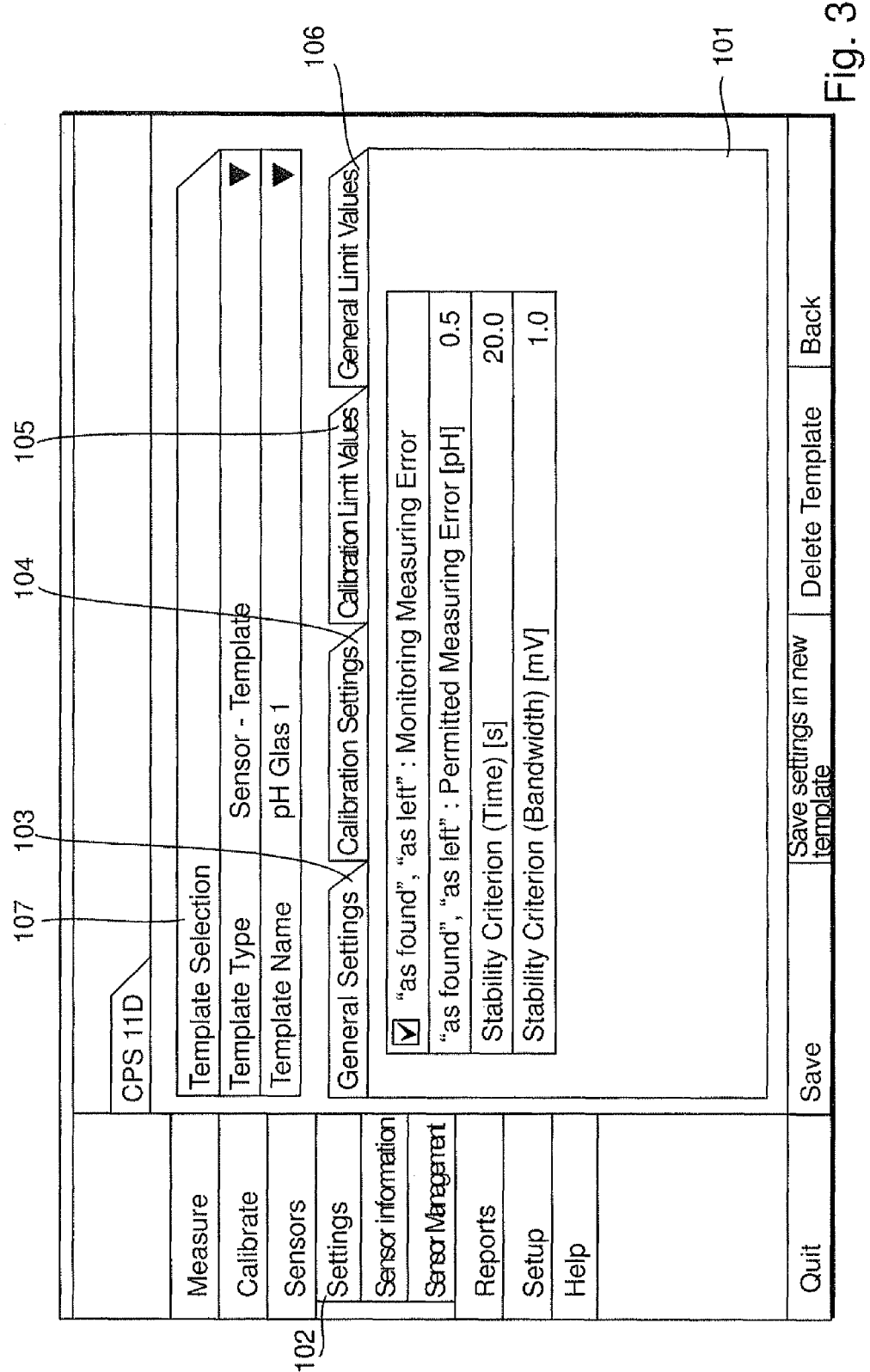
FIG. 3 is a display of a sensor template with predetermined settings for a sensor module.

FIG. 3 shows a screen shot 101 of a display, and entry, form of the operating program; by means of the display, and entry, form, such a template can be created and/or processed. The display, and entry, form can be reached by clicking on the menu option 102 "Settings". The display, and entry, form includes four tabs: "General Settings" 103, "Calibration Settings" 104, "Calibration Limit Values" 105 And "General Limit Values" 106. In the screen shot 101 shown here, the tab "Calibration Settings" 104 is active. There, for example, a desired calibration procedure can be specified for the sensor module or group of sensor modules to which the template is to be applied. Furthermore, it can be specified whether an "as found" measuring should be performed before performing the calibration procedure and an "as left" measuring should be performed before starting up the sensor module again. Moreover, stability criteria can be given, which, as set forth below, are used to end a step of a calibration procedure.

Other specifications for the sensor module or the sensor modules, with which the template is associated, can be made under the additional tabs "General Settings" 107, "Calibration Limit Values" 105 and "General Limit Values" 106. For example, limit values for the parameters zero point and slope of the sensor characteristic line ascertained in a calibration can be fixed. It can be provided e.g. that a warning report be output to the user, in case these limit values are exceeded.

The template so created can be stored in a memory of the control unit or in a central server, which the control unit can access, especially in the database of the measuring system. Each time, when a sensor module, with which the template is associated, is connected to the control unit by means of the interface module, the operating program can ascertain the proper template for this sensor module based on the sensor identification read out from the data memory of the sensor module and take into consideration the corresponding specifications of the template and present them in the display, and entry, form shown in screen shot 101. If a new sensor module, previously not contained in the database, is connected to the control unit, an existing template can be associated with the sensor module by means of a single input into the operating program. If the template is fixed for all sensor modules of a certain sensor type or a certain series designation, the operating program can automatically assign the template to a new sensor module of this sensor type or this specific series designation.

FIG. 4 shows a screen shot 201 of a display, and entry, form for managing sensor modules. Data for the sensor module are presented in the upper area 206; the operating program automatically reads out this data from the data memory of the sensor module or from the database. In the lower area, additional information for the place of installation of the sensor module can be input. In the areas 202, if present, the template is specified, from which the operating program can gather inputs, especially for the calibration procedure to be applied to the sensor module. In areas 203, information for the measuring point, at which the sensor module is applied, can be entered. The information for the measuring point includes, for example, the name of the operation, the plant, with which the sensor module is associated, and/or a special measuring point tag.

In field 204, the standard calibration procedure to be applied for the sensor module, for example, a 1 point or a 2 point calibration, can be selected. In the example shown here this information can be selected from an "open up" menu, also referred to as a drop down menu or pull down menu. In field 205, the user can specify whether, and at which point in time, the operating program should display a reminder for the next scheduled calibration. In addition, there is the opportunity to specify that an automatic reminder should be sent e.g. via email to a stored email address.

The operating program can be embodied, at predetermined points in time, for example, once daily, to create a list of those active sensor modules stored in the database; it is specified for these sensor modules that a reminder for the next calibration should be displayed and for which the next calibration is due within a predetermined time span, for example, within the next three days. Such a list can be delivered to the user via email or be output upon a database query. The list can be sortable by the due date of the next calibration or by measuring point identification. In this way, the managing of the sensors and the organization of the scheduled maintenance measures is facilitated significantly for the user.

In addition to sensor management, the operating program also includes functions for testing means management. Calibration media and reference media are to be understood as examples of testing means. For calibration of pH sensor modules, for example, one or a number of buffer solutions having predetermined pH values are used. For additional "as found"/"as left" measurements, other reference media, which likewise can be buffer solutions, are required.

Figure 5:
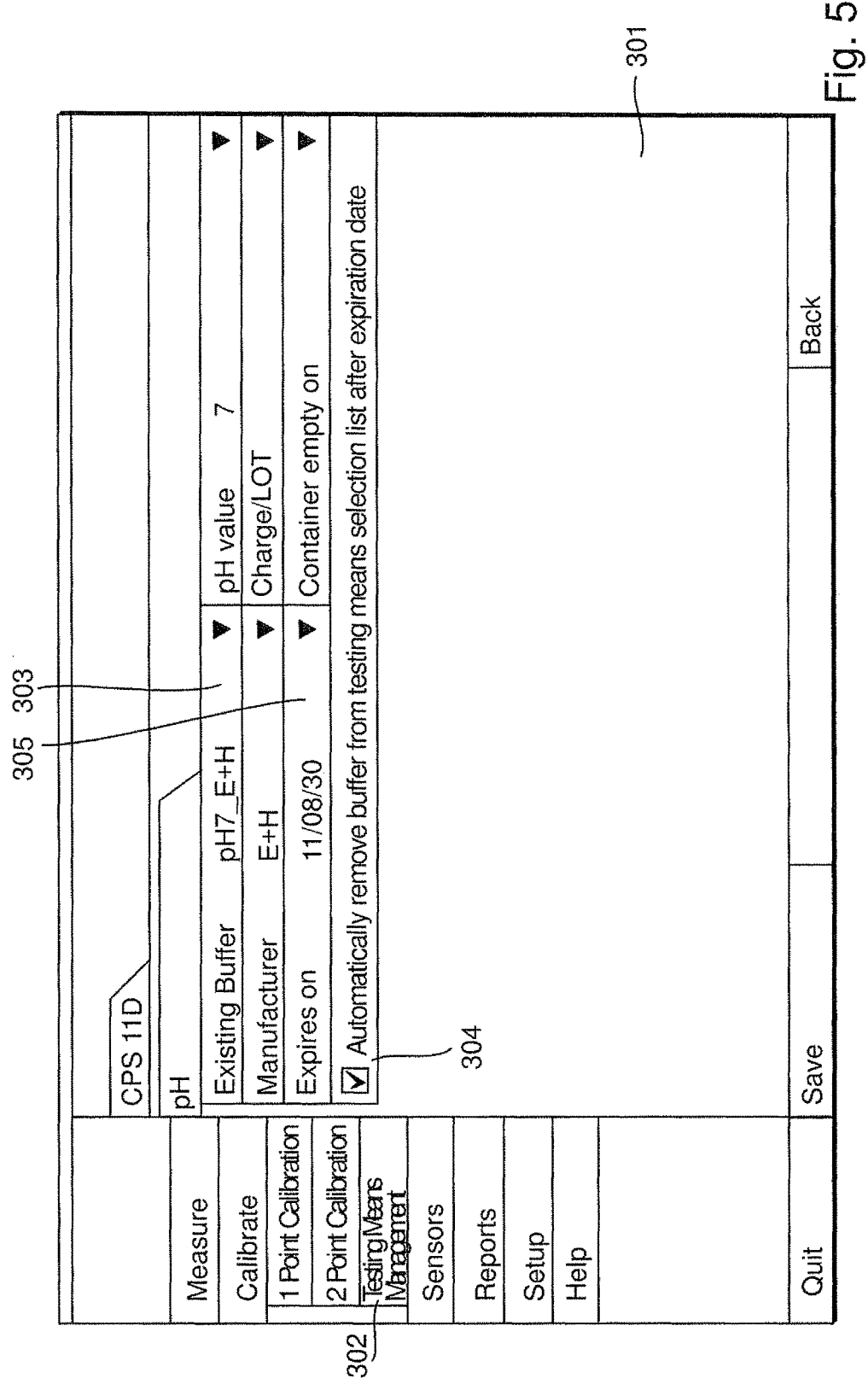
FIG. 5 is a display of the testing means management of the operating program.

FIG. 5 shows a screen shot 301 of a display, and entry, form of the testing means management of the operating program; the display, and entry, form can be invoked via field 302 of the menu bar. Here, testing means already stored in field 303 can be selected or new testing means can be added. In field 305, the expiration date of the testing means can be entered. It can be specified in field 304 that after passing the expiration date of the testing means, the testing means is automatically removed from the testing means selection list in the calibration menu, which is described in greater detail below. If the corresponding box has been checked, the testing means can no longer be selected for a calibration. If the box has not been checked, the corresponding testing means, whose expiration date is exceeded, can at least be highlighted graphically, especially with a color.

Figure 6:
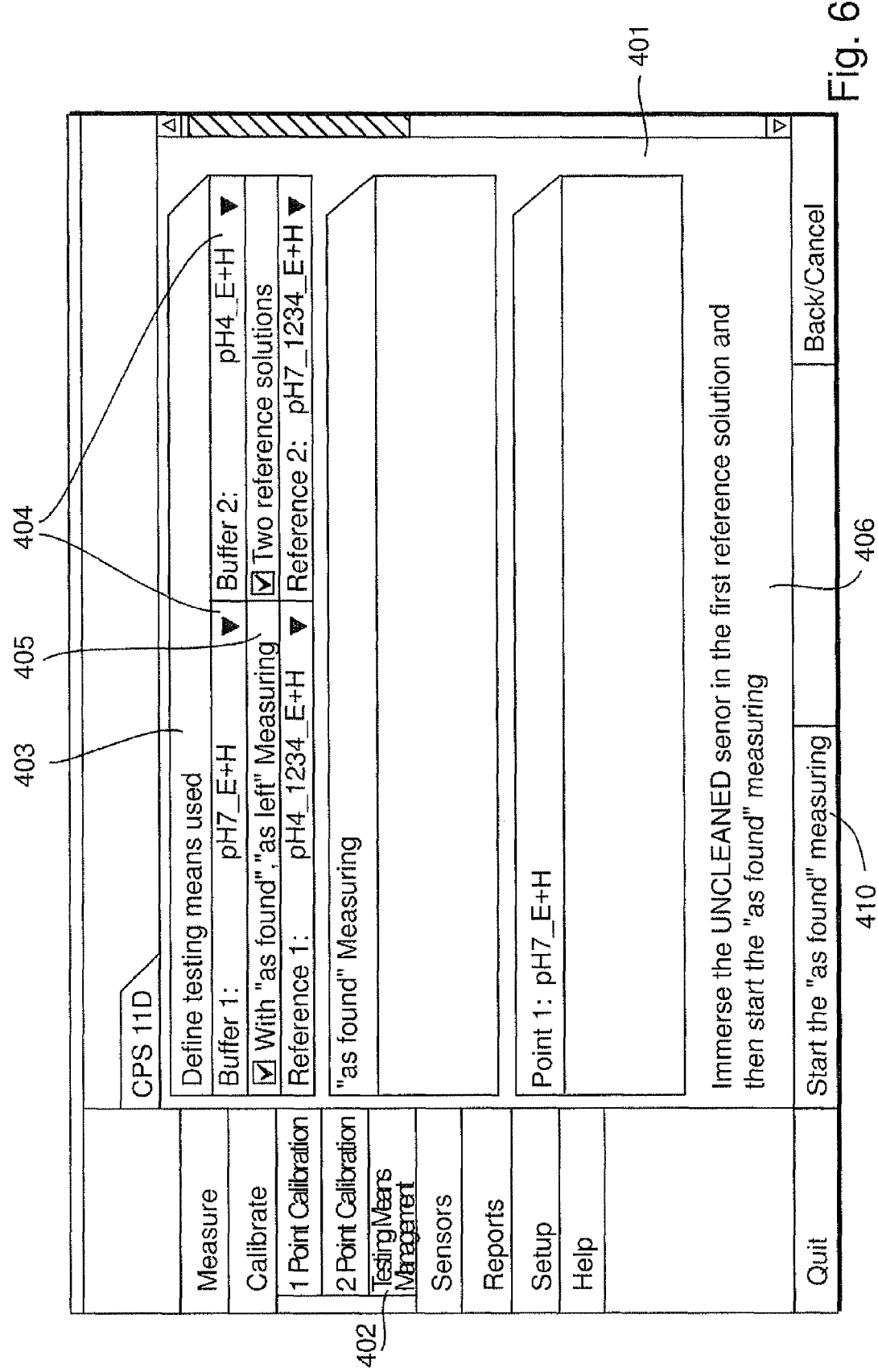
FIG. 6 is a display for calibration of a sensor module by guiding the user through the steps of the calibration procedure in the first step of the calibration procedure.
Figure 7:
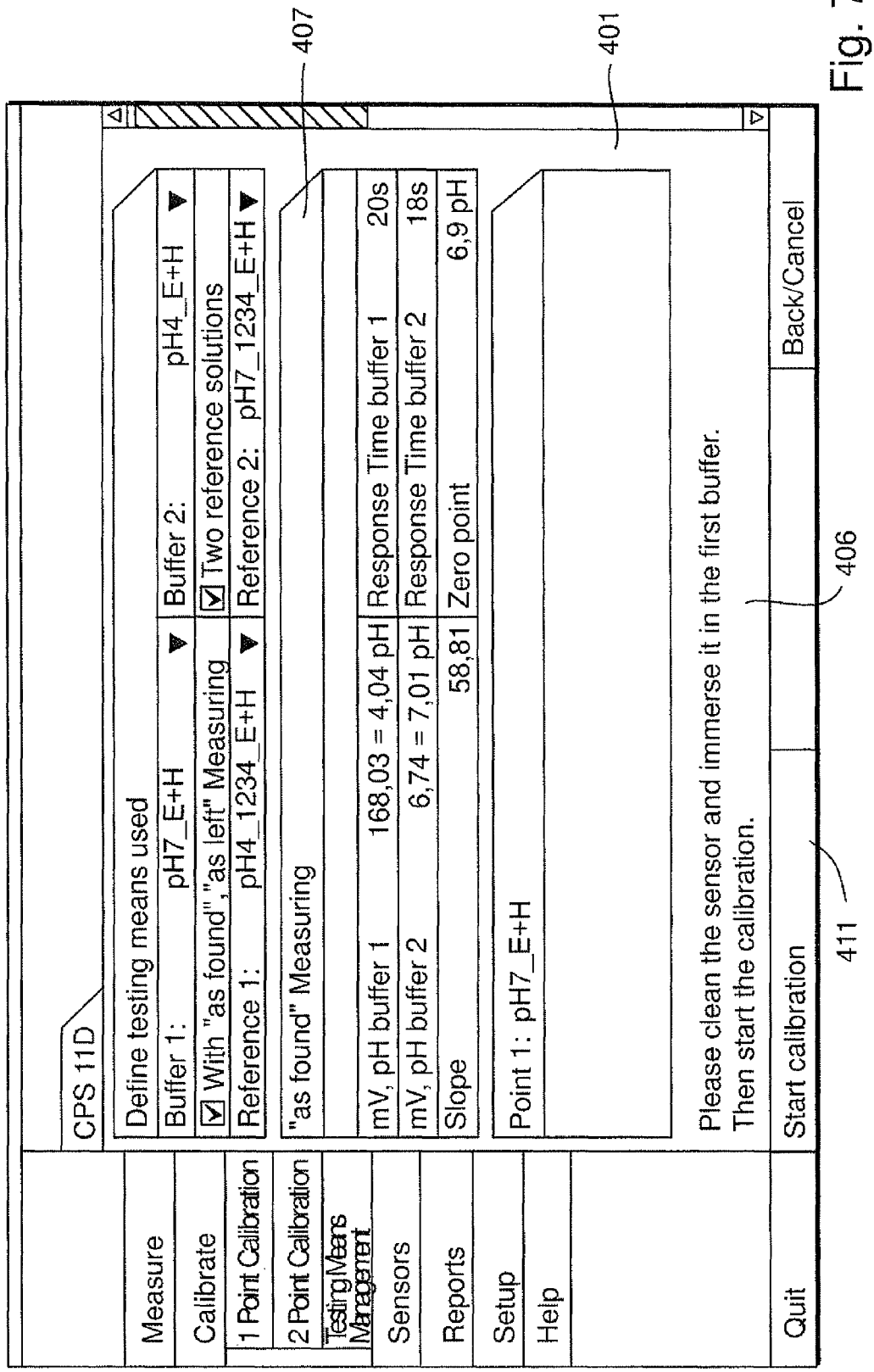
FIG. 7 is the display of FIG. 6 in an additional step of the calibration procedure.
Figure 8:
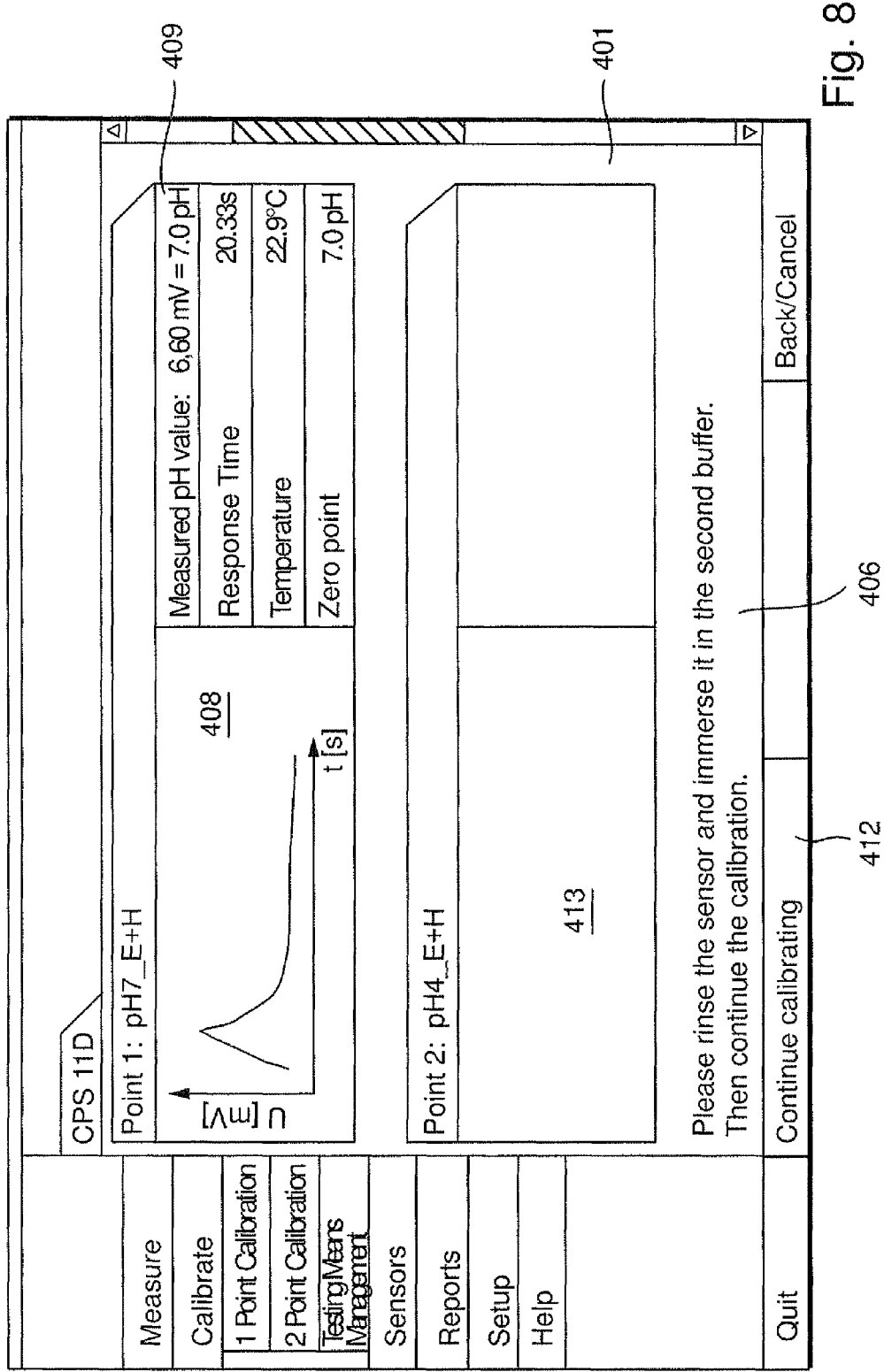
FIG. 8 is the display of FIG. 6 in an additional step of the calibration procedure.

The procedure of a calibration with user guidance by the operating program is presented in FIGS. 6 through 8 based on the example of a 2 point calibration of a pH sensor module beginning with an "as found" measuring and terminating with an "as left" measuring. By choosing menu option 402 in the menu bar of the operating program, the user can invoke the display, and entry, form shown in screen shot 401 for performing a calibration of the connected sensor module. In a first step, the user is requested in field 403 to define the testing means to be used. For a 2 point calibration of a pH sensor module, two buffer solutions having different pH values are required. These buffer solutions can be selected via the pull down menus 404. Pull down menus 404 offer the user only those testing means stored in the database suitable for calibration of the currently connected sensor module. If the box has been checked in the testing means management that testing means, whose expiration date is exceeded, should not be selectable in the calibration menu, such testing means are no longer displayed in pull down menu 404 after the exceeding of the expiration date. If the box has not checked, those testing means, whose expiration date is exceeded, are displayed; however, they are graphically highlighted, for example, with color.

In the fields 405, the user must indicate the reference media for the "as found" measuring and the "as left" measuring. Only when these inputs have been made can the "as found" measuring be started.

In the field 406, an operating instruction for performing the next required step of the calibration procedure, highlighted with a color, is displayed to the user. In the example described here, the user is requested to immerse the uncleaned sensor into the first reference solution and start the "as found" measuring. By clicking on the field 410 "start as found measuring", the user can start the measuring.

The screen shot shown in FIG. 7 shows display, and entry, form 401 after termination of the "as found" measuring. The measurement results of the measurements performed in the first and second reference solutions, the response times, as well as the values of the slope and the zero point of the characteristic line of the sensor module derived from these measurement results are displayed in the area 407.

In field 406, the user is now requested to clean the sensor, to submerge it in the first calibration medium and, thereafter, to start the first calibration measurement. The calibration measurement can be started by clicking on the field 411 "start calibration".

The screen shot shown in FIG. 8 shows display, and entry, form 401 after terminating the first calibration measurement in the first calibration medium, which is a buffer solution with a pH value 7 in the example shown here. The measured value curve is graphically presented as a function of time in the window 408 during the calibration measurement. This information can allow experienced users to make deductions on the state of the sensor and on regeneration measures possibly required. The first calibration measurement is continued until the measured value output by the sensor module fulfills the stability criteria established in the template associated with the sensor module (see FIG. 3). As soon as fulfillment of the stability criteria is detected, the operating program automatically ends the first calibration measurement and shows the results of the first calibration measurement in area 409. In the example shown here, the pH value measured in the first calibration medium, the response time, the temperature and the zero point are displayed in area 409.

The next step of the calibration procedure includes a second calibration measurement in a second calibration medium having a second pH value different from the pH value of the first calibration medium. In field 406 the user is requested to rinse the sensor and immerse it in the second calibration medium. The user can continue the calibration by clicking on the field 412.

During the second calibration measurement, just as in the first calibration measurement, the measured value curve is graphically presented in the window 413 as a function of time. The second calibration measurement is continued until the measured value output by the sensor module fulfills the stability criteria specified in the template associated with the sensor module. As soon as the fulfillment of the stability criteria is detected, the operating program automatically ends the second calibration measurement and displays the results of the second calibration measurement fields (not shown here) in an area next to window 413. Furthermore, the values for the zero point and slope of the characteristic line of the sensor module ascertained from the calibration measurements are displayed.

The user can choose whether an adjustment of the sensor module should be performed based on the results of the first and second calibration measurements. For adjustment of the sensor module, the zero point and the slope of the characteristic line of the sensor module are stored in the data memory of the sensor module. These values are also simultaneously stored in the database. The values of the zero point and slope ascertained in earlier adjustments are, in such case, not over written, but remain stored in the database and/or in the data memory of the sensor module, coordinated with the point in time of the respective calibration.

Finally, an "as left" measuring can be performed with the adjusted sensor. This runs in an analogous manner to the "as found" measuring described above. In the "as left" measuring, the operating program guides the user through the individual method steps.

All results of the calibration measurements and the adjustings are stored in the database with reference to the sensor module currently connected. The results are supplementally stored in the data memory of the sensor module. In an alternative embodiment of the operating program, the user can select whether the results of the calibration measurements and adjustments are stored only in the database, only in the data memory of the sensor module or in both the database as well as the data memory of the sensor module. It can also be provided that the user can specify for particular individual data whether the data should be stored in the database and/or the data memory of the sensor module.

Figure 9:
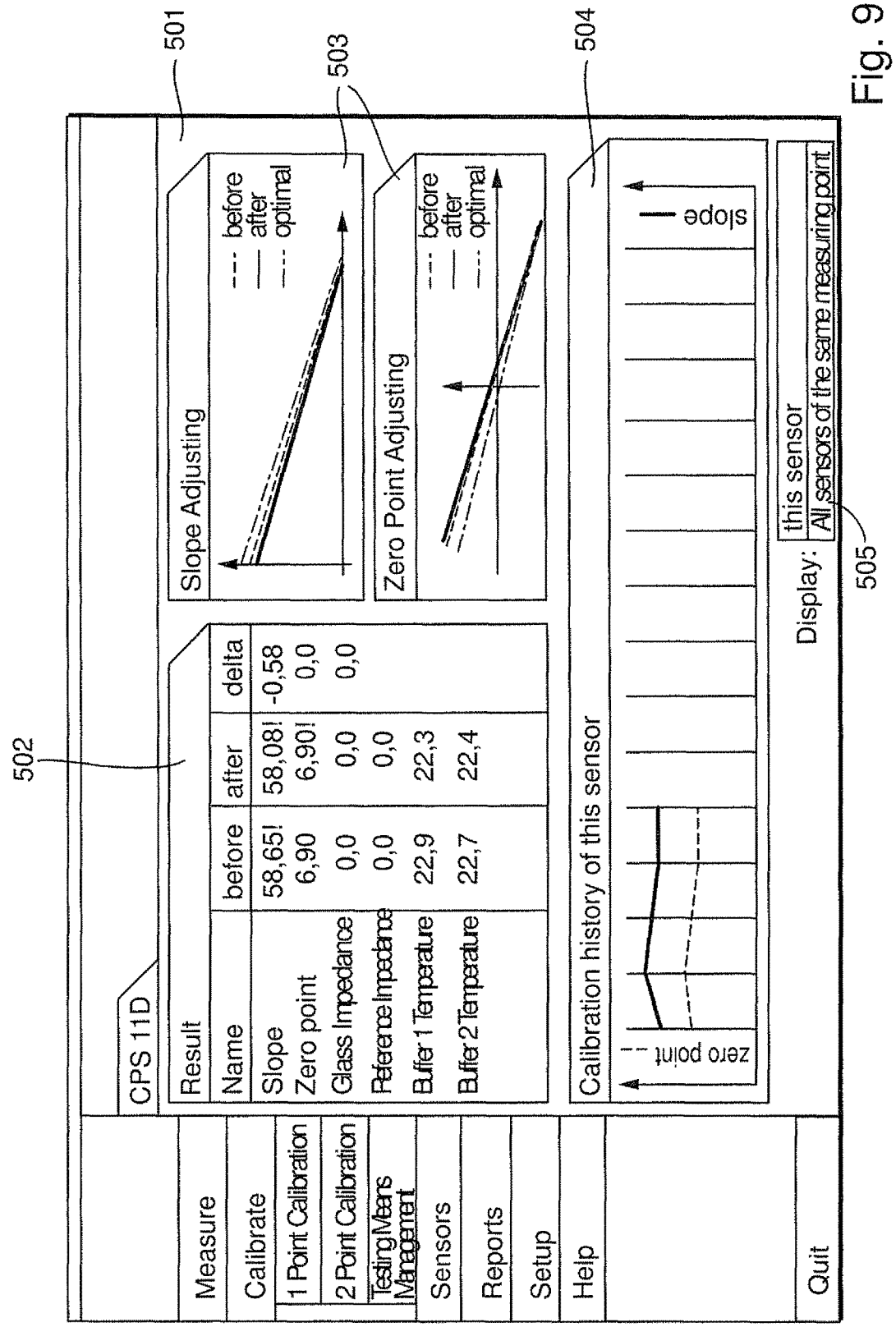
FIG. 9 is a display of a calibration result.

FIG. 9 shows another screen shot 501 of a display, and entry, form of the operating program; the result of the calibration and/or adjusting performed earlier is presented in detail in the display, and entry, form. The result of the calibration, especially the slope and the zero point of the characteristic line of the sensor module ascertained from the calibration measurements, and the differences relative to the zero point and slope ascertained in the preceding calibration of the sensor module are presented in the area 502. The operating program can be embodied to compare the newly ascertained zero point and the newly ascertained slope with a tolerance interval of the zero point and slope specified in the sensor management described above. If one of the interval boundaries of the stored tolerance intervals is exceeded, the corresponding value of the zero point or the slope is highlighted graphically, for example, by an exclamation point or by a colored emphasis.

In addition to the results for the zero point and slope, the temperatures of the calibration media used in the calibration measurements and/or other diagnostic information, for example, the impedance of the glass membrane in a pH sensor module, can be displayed in area 502.

A graphical representation of a comparison between the characteristic line of the sensor module before the current calibration, the new characteristic line of the sensor module ascertained from the current calibration results and an ideal characteristic line is presented in areas 503.

In area 504, the calibration history of the sensor module is illustrated by curves for the zero points ascertained in past calibrations and the slopes ascertained in past calibrations graphically presented as a function of time. By means of the menu 505, a representation of the calibration history of all sensors at the same measuring point can also be selected. From such a representation, a user can make deductions on the influence of the measuring point on the aging of the sensor modules.

The detailed calibration result shown in screen shot 501 can be seen before the adjustment of the sensor module. In this way, a user can determine whether an adjustment of the sensor module is even worthwhile, based on the detailed calibration result before the adjustment.

For each sensor module, which is connected to the control unit via the interface module, an entry is generated in the database; this entry includes the name of the sensor and an identification of the sensor module, for example, an order code or a serial number. All data contained in the data memory of the sensor module and read out by the control unit by means of the operating software are stored with this sensor identification. Additionally, data input by a user via the entry forms of the operating software for the sensor module are stored in the database. Also, the results of calibration measurements as well as the parameters of the characteristic line of the sensor module, for example, the zero point and slope, ascertained from the calibration measurements are stored in the database together with the point in time of the calibration and, respectively, adjusting. Especially, the database contains the date of manufacture of a sensor module, the measuring point designation, limit values for the measurement parameters of the sensor module, temperature limit values, the settings of the sensor template mentioned above, results of calibration measurements, the values of the zero point and slope of the characteristic line ascertained in different calibrations, as well as the results of "as found"/"as left" measurements.

The operating program is embodied to create, upon an input of the user, a report, i.e. a computer file, especially a printable document, in which certain data are compiled from the data stored in the database at any point in time. For example, the operating program can create a calibration report containing the current calibration results, a comparison of the current calibration results with the results of the previous calibration and, if desired, a calibration history, especially a graphical representation of the calibration history. Similarly, the operating program can create a sensor report containing information for a selected sensor module, for example, the currently connected sensor module. The sensor report can especially include data for predictive maintenance, diagnostic data and a prediction of the remaining life of the sensor module.

If a new sensor module is connected to the control unit via the interface module, the operating program can perform a comparison of the data read out from the data memory of the sensor module with the data stored in the database for this sensor module. If the sensor module is unknown, a new database entry is generated and the read out data entered into the database. If the sensor module is known, i.e. already entered in the database, but the data memory of the sensor module contains, for example, calibration data not contained in the database, these data are, in given cases, transferred to the database, after confirmation by the user. This situation can arise in sensor modules, which are not calibrated exclusively by means of the measuring system described here, but are also calibrated from time to time by means of a measurement transmitter directly on-site at the measuring point, at which the sensor module is applied. By inputting the results of such calibrations into the database, a gapless calibration history can be provided.

The invention claimed is:

1. A measuring system, comprising:
a control unit, the control unit having a display apparatus and an input system;
at least one sensor module, each sensor module having a measuring transducer and an electronics module, the electronics module having a data memory in which sensor-specific data are stored, the sensor-specific data comprising at least a sensor identification; and
at least one interface module, wherein:
each sensor module is connected to the control unit via its corresponding interface module, the connection being a measurement channel,
each interface module includes signal processing and communication electronics embodied to convert received signals from the at least one sensor module into signals processable by the control unit, to output these signals to the control unit, to convert received signals from the control unit into signals processable by the at least one sensor module, and to output these signals to the at least one sensor module,
the control unit is embodied to execute an operating program for the at least one sensor module,
the operating program is configured to enable a user to specify attributes of a calibration procedure and to store a plurality of calibration procedures for a sensor module or for a group of sensor modules,
the operating program is further configured to read out sensor-specific data from the data memory of the at least one sensor module and, based on the sensor identification, to identify more than one stored calibration procedure for the at least one sensor module, to present to the user a selection menu when more than one stored calibration procedure is identified for the at least one sensor module, to enable the user to select one of the stored calibration procedures in the selection menu, to guide the user through a sequence of steps for performing the selected calibration procedure associated with the at least one sensor module, and to operate the at least one sensor module for performing the calibration procedure,
the operating program is further configured to operate the measurement channels in parallel, and
the operating program is multiply instantiable and each instance of the operating program is embodied for servicing one of said plurality of sensor modules, so that the plurality of sensor modules can be serviced simultaneously.

2. The measuring system as claimed in claim 1, wherein upon an input by the user, the operating program performs a calibration procedure of the following steps:
displaying a request to specify a first and a second calibration medium;
displaying a request to clean the sensor module and to bring the sensor module in contact with the first calibration medium;
performing a first calibration measurement;
displaying and storing a first calibration data of the first calibration measurement after terminating the first calibration measurement;
displaying a request to bring the sensor module in contact with the second calibration medium;
performing a second calibration measurement; and
displaying and storing a second calibration data of the second calibration measurement after terminating the second calibration measurement.

3. The measuring system as claimed in claim 2, wherein:
said operating program is embodied to determine a zero point and/or a slope of a characteristic line of said sensor module based on the first and second calibration measurements and to store the zero point and/or slope of a characteristic line of said sensor module in a database and/or the data memory of said sensor module.

4. The measuring system as claimed in claim 2, wherein:
said operating program is embodied, in the case of selection of a calibration procedure with an "as found"/"as left" measuring, before performing the calibration, to prompt the user to perform a first measuring in at least one reference medium, and, after performing the calibration and adjusting of said sensor module, to perform a second measuring in said at least one reference medium; and
the results of the first and second measurements in the at least one reference medium are stored in a database.

5. The measuring system as claimed in claim 2, wherein:
performing said first calibration measurement and/or said second calibration measurement upon an input by the user.

6. The measuring system as claimed in claim 2, wherein:
displaying and storing calibration measured value, response time, temperature of the calibration medium and point in time of the first calibration measurement after terminating the first calibration.

7. The measuring system as claimed in claim 2, wherein:
displaying and storing calibration measured value, response time, temperature of the calibration medium and point in time of the second calibration measurement after terminating the second calibration.

8. The measuring system as claimed in claim 1, further comprising:
a database, wherein:
said operating program is embodied to access data stored in said database and/or to store data in said database.

9. The measuring system as claimed in claim 8, wherein:
said operating program includes an entry form serving to manage sensor modules;
information concerning and specifications for individual sensor modules and/or for a group of sensor modules can be input into said entry form; and
all such information already contained in the data memory of said sensor module is read out automatically by said operating program and is automatically displayed in fields provided therefor in said entry form.

10. The measuring system as claimed in claim 8, wherein:
said operating program is embodied to create a list based on information stored in said database for sensor management; and
sensor modules to be calibrated next in time as well as the next calibration point in time for these sensor modules are stated in the list.

11. The measuring system as claimed in claim 10, wherein:
said operating program is embodied to transmit the list to a stored email address or to another system usable for this purpose.

12. The measuring system as claimed in claim 1, wherein:
said operating program is embodied, upon request by the user, to compile data and/or data histories stored in a database and/or in the memory of the connected sensor module in a report, and to output such report as a storable and/or printable file.

13. The measuring system as claimed in claim 12, wherein:
said report is a sensor report or calibration report.

14. The measuring system as claimed in claim 1, wherein:
said operating program is embodied to display, curves of zero point and slope of the characteristic line of a sensor module or a group of sensor modules, which are associated with a certain measuring point.

15. The measuring system as claimed in claim 14, wherein:
said operating program is embodied to display curves of zero point and slope of the characteristic line of all sensor modules which are associated with a certain measuring point.

16. The measuring system as claimed in claim 1, wherein:
said operating program is embodied to operate said at least one sensor module in a measurement operation;
the user can choose between a continuous measuring operation and a standard measurement operation, in which a measuring interval with a beginning point and end point in time is predeterminable.

17. The measuring system as claimed in claim 16, wherein:
said operating program is embodied to present measured value development in a 2 or 3 dimensional graph in measurement operation.

18. The measuring system as claimed in claim 1, wherein:
at least two sensor modules are embodied for measuring different parameters.

19. The measuring system as claimed in claim 1, wherein:
at least one of the steps for performing a calibration procedure requires an input by the user by means of said input system; and
said operating program is embodied, upon the input, to operate said sensor module.

20. The measuring system as claimed in claim 1, wherein the calibration procedure includes performing at least one calibration measurement with the sensor module in a calibration medium and
the operating program displays a measurement signal output by the sensor module during the calibration procedure as a function of time.

21. The measuring system as claimed in claim 1, wherein:
said operating program is embodied, in the case of connecting a sensor module via said interface module to said control unit, to compare calibration data stored in said sensor module with calibration data for this sensor module stored in a database and, upon finding unknown calibration data, to record such in said database.

22. The measuring system as claimed in claim 1, wherein:
specification of at least one calibration medium for a calibration procedure occurs by selecting a calibration medium from a calibration media list;
said operating program includes an entry form for managing calibration media;
a calibration media designation, an expiration date of the calibration medium and, other information for each calibration medium are input into said entry form; and
it is specified that, after exceeding the expiration date of the calibration medium, the calibration medium should be automatically removed from the calibration media list or alternatively be made specially noticeable.

\* \* \* \* \*